United States Patent
Montpetit et al.

(10) Patent No.: US 7,393,320 B2
(45) Date of Patent: Jul. 1, 2008

(54) PELVIC FLOOR HEALTH ARTICLES AND PROCEDURES

(75) Inventors: Karen Pilney Montpetit, Mendota Heights, MN (US); James E. Cox, Corcoran, MN (US); Kimberly A. Anderson, Eagan, MN (US)

(73) Assignee: AMS Research Corporation, Minnetonka, MN (US)

( * ) Notice: Subject to any disclaimer, the term of this patent is extended or adjusted under 35 U.S.C. 154(b) by 86 days.

(21) Appl. No.: 11/413,285

(22) Filed: Apr. 28, 2006

(65) Prior Publication Data

US 2006/0258898 A1    Nov. 16, 2006

Related U.S. Application Data

(60) Provisional application No. 60/676,477, filed on Apr. 29, 2005.

(51) Int. Cl.
  *A61F 2/02* (2006.01)
(52) U.S. Cl. ......................................................... 600/30
(58) Field of Classification Search ......... 128/897–898; 57/243; 600/29–37; 602/44; 604/273, 274, 604/263; 606/37, 72, 119, 139, 141, 144, 606/145, 146, 148, 151, 167, 185, 222, 223, 606/224, 225, 232
  See application file for complete search history.

(56) References Cited

U.S. PATENT DOCUMENTS

| | | | |
|---|---|---|---|
| 5,112,344 A | 5/1992 | Petros | |
| 5,611,515 A | 3/1997 | Benderev et al. | |
| 5,842,478 A | 12/1998 | Benderev et al. | |
| 5,860,425 A | 1/1999 | Benderev et al. | |
| 5,899,909 A | 5/1999 | Claren et al. | |
| 6,039,686 A | 3/2000 | Kovac | |
| 6,042,534 A | 3/2000 | Gellman et al. | |
| 6,080,116 A * | 6/2000 | Erickson et al. | 600/573 |
| 6,110,101 A | 8/2000 | Tihon et al. | |
| 6,273,852 B1 | 8/2001 | Lehe et al. | |
| 6,478,727 B2 | 11/2002 | Scetbon | |
| 6,612,977 B2 | 9/2003 | Staskin et al. | |
| 6,638,211 B2 | 10/2003 | Suslian et al. | |
| 6,641,525 B2 | 11/2003 | Rocheleau et al. | |
| 6,908,425 B2 | 6/2005 | Luscombe | |
| 6,911,003 B2 | 6/2005 | Anderson et al. | |
| 6,932,759 B2 | 8/2005 | Kammerer et al. | |

(Continued)

FOREIGN PATENT DOCUMENTS

WO    WO 96/06567    3/1996

(Continued)

OTHER PUBLICATIONS

American Medical Systems website, Monarc™ Subfascial Hammock, pp. 1-2, 2005.

(Continued)

*Primary Examiner*—Charles A. Marmor, II
*Assistant Examiner*—Christine D Hopkins
(74) *Attorney, Agent, or Firm*—Jose' W. Jimenez; Kimberly K. Baxter; Gregory L. Koeller

(57) ABSTRACT

Articles and procedures for preventing or treating vaginal prolapse, urinary incontinence, and other disorders of the pelvic floor.

3 Claims, 6 Drawing Sheets

U.S. PATENT DOCUMENTS

| | | |
|---|---|---|
| 6,960,160 B2 | 11/2005 | Browning |
| 6,991,597 B2 | 1/2006 | Gellman et al. |
| 7,037,255 B2 | 5/2006 | Inman et al. |
| 7,083,568 B2 | 8/2006 | Neisz et al. |
| 7,112,171 B2 | 9/2006 | Rocheleau et al. |
| 7,131,943 B2 | 11/2006 | Kammerer |
| 2002/0007222 A1 | 1/2002 | Desai |
| 2002/0077526 A1* | 6/2002 | Kammerer et al. ............ 600/30 |
| 2002/0099258 A1* | 7/2002 | Staskin et al. ................. 600/29 |
| 2002/0147382 A1 | 10/2002 | Neisz et al. |
| 2002/0156489 A1* | 10/2002 | Gellman et al. ............ 606/139 |
| 2002/0188169 A1 | 12/2002 | Kammerer et al. |
| 2003/0032929 A1* | 2/2003 | McGuckin, Jr. ............. 604/272 |
| 2003/0130670 A1 | 7/2003 | Anderson et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0233108 A1* | 12/2003 | Gellman et al. ............ 606/144 |
| 2004/0006353 A1 | 1/2004 | Bosley, Jr. et al. |
| 2004/0039453 A1 | 2/2004 | Anderson et al. |
| 2004/0087970 A1 | 5/2004 | Chu et al. |
| 2004/0225181 A1 | 11/2004 | Chu et al. |
| 2004/0230206 A1 | 11/2004 | Gellman et al. |
| 2004/0230207 A1 | 11/2004 | Gellman et al. |
| 2005/0037132 A1 | 2/2005 | Horres et al. |
| 2005/0075660 A1* | 4/2005 | Chu et al. ................... 606/190 |
| 2005/0080317 A1 | 4/2005 | Merade |
| 2005/0131393 A1 | 6/2005 | Chu et al. |
| 2005/0143618 A1 | 6/2005 | Anderson et al. |
| 2005/0245787 A1 | 11/2005 | Cox et al. |
| 2005/0250977 A1 | 11/2005 | Montpetit et al. |
| 2006/0041185 A1 | 2/2006 | Browning |
| 2006/0058574 A1 | 3/2006 | Priewe et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0141861 A1 | 6/2006 | Darley et al. |
| 2006/0195011 A1 | 8/2006 | Arnal et al. |
| 2006/0229493 A1 | 10/2006 | Weiser et al. |
| 2006/0260618 A1 | 11/2006 | Hodroff et al. |
| 2007/0015953 A1 | 1/2007 | MacLean |

FOREIGN PATENT DOCUMENTS

| | | | |
|---|---|---|---|
| WO | WO 97/13465 | | 4/1997 |
| WO | WO 99/59477 | | 11/1999 |
| WO | WO01/89440 A | * | 11/2001 |
| WO | WO 02/39890 | | 5/2002 |
| WO | WO 02/069781 | | 9/2002 |
| WO | WO 03/013392 | | 2/2003 |
| WO | WO 2005/037132 | | 4/2005 |
| WO | WO 2005/107606 | | 11/2005 |
| WO | WO 2006/041861 | | 4/2006 |

OTHER PUBLICATIONS

American Medical Systems website, Monarc™ Subfascial Hammock, p. 1, 2005.

American Medical Systems website, Apogee™ Vaginal Vault Prolapse Repair System, p. 1, 2005.

American Medical Systems website, Perigee™ Prolapse Repair System, p. 1, 2005.

American Medical Systems website, SPARC™ Self-Fixating Sling System, pp. 1-2, 2005.

American Medical Systems website, SPARC™ Sling System, pp. 1-2, 2005.

* cited by examiner

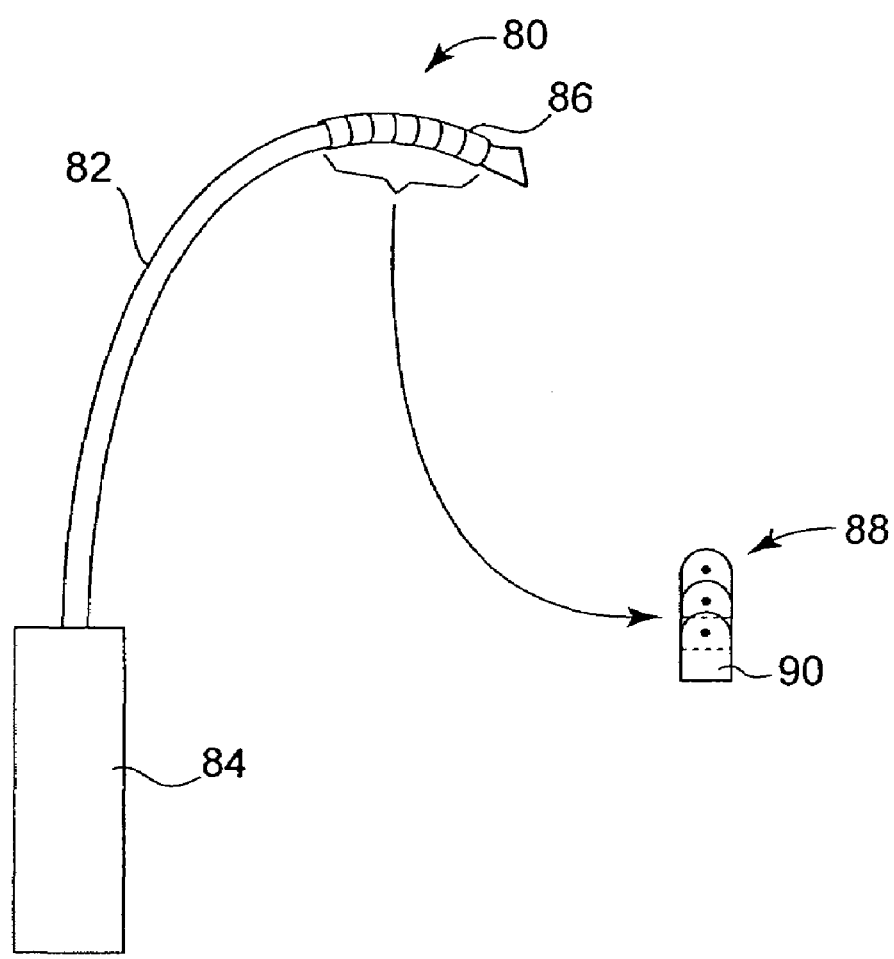
Fig. 5
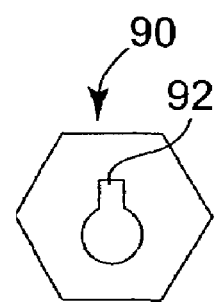
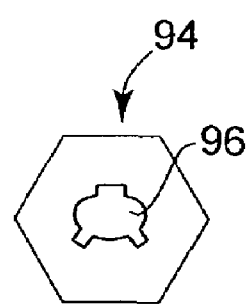
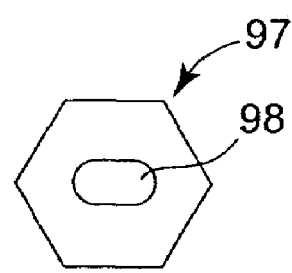
Fig. 6a      Fig. 6b      Fig. 6c

PELVIC FLOOR HEALTH ARTICLES AND PROCEDURES

CROSS-REFERENCE TO RELATED APPLICATION

The present application claims priority to U.S. Provisional Application No. 60/676,477, filed Apr. 29, 2005, the entire contents of which are incorporated herein by reference in its entirety.

TECHNICAL FIELD

The present invention relates to articles and procedures for preventing or treating vaginal prolapse, urinary incontinence, and other disorders of the pelvic floor.

BACKGROUND

In a normal female body, the levator ani muscles close the pelvic floor and support the vagina. This results in little force being applied to the fascia and ligaments that support the vagina. Increases in abdominal pressure, failure of the muscles to keep the pelvic floor closed, and damage to ligaments and fascia can all contribute to the development of prolapse. Vaginal prolapse changes the position of the vagina, which can lead to discomfort, urinary incontinence, and incomplete emptying of the bladder. In severe cases, vaginal prolapse conditions can even cause the vagina to become positioned outside of the body. One specific type of prolapse is referred to as posterior vaginal prolapse, which may additionally cause defecatory problems such as tenesmus and difficulty in stool evacuation. Conditions of posterior vaginal wall prolapse can involve descent of the rectum into the vagina, often termed a rectocele, or the presence of small intestine in a hernia sac between the rectum and vagina, called an enterocele.

Broadly, there are four types based on suspected etiology. Congenital enteroceles are thought to occur because of failure of fusion or reopening of fused peritoneal leaves down to the perineal body. Post-hysterectomy vault prolapse can result from a lack of support from detachment of the uterosacral ligaments from the uterus at the time of hysterectomy. Enterocele may occur because of failure to reapproximate the superior aspects of the pubocervical fascia and the rectovaginal fascia at the time of a surgery. Iatrogenic prolapse may occur after a surgical procedure that changes the vaginal axis, such as certain surgical procedures for treatment of incontinence. With regard to rectoceles, the most common type of rectocele results from disruption of connective tissue supports of the rectovaginal fascia from its normal attachments to the uterosacral ligaments. Posterior or post-hysterectomy enteroceles may accompany rectoceles.

Several factors have been implicated as being involved in causing vaginal prolapse. It is thought that individual women have differing inherent strength of the relevant connective tissue. Further, loss of connective tissue strength might be associated with damage at childbirth, deterioration with age, poor collagen repair mechanisms, and poor nutrition. Loss of muscle strength might be associated with neuromuscular damage during childbirth, neural damage from chronic straining, and metabolic diseases that affect muscle function. Other factors involved in prolapse include increased loads on the supportive system as seen in prolonged lifting or chronic coughing from chronic pulmonary disease, or some disturbance in the balance of the structural support of the genital organs. Obesity, constipation, and a history of hysterectomy have also been implicated as possible factors. In particular, the vaginal angle may be altered upon removal of the uterus in a hysterectomy, causing increased pressure at a more acute angle and thereby accelerating the prolapse.

Various techniques have been used to attempt to correct or ameliorate prolapse and prolapse symptoms, with varying degrees of success. Nonsurgical treatment of prolapse involves measures to improve the factors associated with prolapse, including treating chronic cough, obesity, and constipation. Vaginal pessaries are the primary type of nonsurgical treatment, but potential complications can occur such as vaginal wall ulceration. Other nonsurgical treatments may include pelvic muscle exercises or supplementation with estrogen. These therapies may alleviate some symptoms and temporarily provide some relief to the patient, but any actual hernia will remain.

Surgical treatments of posterior prolapse can involve vaginal and abdominal procedures to reapproximate the attenuated tissue using sutures or a biological or synthetic implant to provide continuing support of the reapproximated tissue following the procedure. Implants that have been used to address pelvic organ prolapse are described, for example, in U.S. Patent Publication No. 2004/0039453, entitled "Pelvic Health Implants and Methods", and U.S. Patent Publication No. 2005/0245787, entitled "Method and Apparatus for Treating Pelvic Organ Prolapse", which patent applications are incorporated entirely herein by reference.

An example of a specific implant product designed for treating conditions of vaginal vault prolapse is a product commercially available from American Medical Systems, Inc., of Minnetonka, Minn. under the trade designation "APOGEE". Very generally, devices of this type are designed to be implanted in a manner to support vaginal tissue. These devices and similar products can include various designs, such as "strips" of a single material or pieces of the same or different materials connected together (e.g., mesh, tape, optionally including synthetic or biological tissue portions) to form an implant that can be attached at one portion to vaginal tissue, with another portion attached at a position of the anatomy that supports the vaginal tissue.

Another pelvic floor disorder that can occur in patients is referred to as urinary incontinence or involuntary loss of urinary control, which is a problem that afflicts men, women, and children of all ages. A variety of treatment options for incontinence are currently available. Some of these include external devices, behavioral therapy (such as biofeedback, electrical stimulation, or Kegel exercises), and prosthetic devices. Depending on the age, medical condition, and personal preference of a patient, surgical procedures can additionally or alternatively be used to completely restore continence.

One type of surgical procedure found to be an especially successful treatment option for incontinence in both men and women is a referred to as a sling procedure. Sling procedures typically entail surgically implanting a biocompatible implant or "sling" to support the bladder neck or urethra in manners that are somewhat similar to those described above for prolapse correction techniques. Sling procedures are discussed in U.S. Pat. Nos. 5,112,344; 5,611,515; 5,842,478; 5,860,425; 5,899,909; 6,039,686; 6,042,534; 6,110,101; 6,478,727; 6,638,211; and PCT Publication Nos. WO 02/39890 and WO 02/069781, for example.

Some "pubomedial" sling procedures involve an abdominal incision and installation of a sling between the rectus fascia in the abdominal region to a position below the urethra, and back again to the rectus fascia. A conventional procedure in females is to surgically place a sling by entering the abdominal cavity through an incision in the patient's pubovaginal region. In males, one exemplary conventional method involves surgical placement of a sling by entering the abdominal cavity through an abdominal incision.

Other methods for treating pelvic conditions involve installation of a sling below the urethra through incisions made at the inner thigh (e.g., in the perineal skin facing the obturator and in the groin), and using a tissue path extending through the obturator. These procedures can be referred to as "transobturator" methods, which are described, for example, in U.S. Pat. No. 6,911,003 and U.S. Patent Publication Nos. 2003/0171644 and 2005/0143618, the entireties of each being incorporated herein by reference.

While these described devices and methods of treating urinary incontinence and vaginal prolapse can be effective, safe, and long-lasting, there is ongoing effort toward improving these devices and methods.

SUMMARY

One aspect of the invention relates to methods of treating urinary incontinence by surgical implantation of a urethral sling through a tissue path that traverses the obturator foramen. These "transobturator" methods generally involve two lateral incisions at the inner thigh, each near a patient's obturator foramen, and a third, medial incision at the perineum. An elongate sling is implanted between the medial incision and the two lateral incisions, with opposing end portions of the sling traversing each obturator foramen. The slings include a variety of tips or dilator configurations at the end of the extension portions of the sling for connecting to the tips of their corresponding implantation tool or tools.

The sling can include two opposing elongate end portions that pass through each obturator foramen and a central support portion that is placed to support the urethra, below the urethra but not necessarily in contact with the urethra. The central support portion can be adapted for contacting and supporting a pelvic tissue. A central support portion of the sling can be placed in contact with tissue below the urethra and tensioned to support pelvic tissue including the urethra, to improve continence.

The steps of a transobturator method can include, for example, implanting a urethral sling with end portions of the sling passing through the obturator, and then positioning and tensioning of a central support portion of the sling to approximate or support tissue of the pelvic region such as tissue of the urethra and related pelvic tissue. Continence can be improved by approximating pelvic tissue optionally to re-align or improve the alignment or positioning of the urethra relative to the rhabdosphincter. Desirably, the sling can be tensioned to approximate and lift the urethra (e.g., posterior urethra) proximally, toward the bladder, and place or return the urethra to an anatomically normal position, improving sphincter functioning, coaptation of the urethra, and continence.

A useful urethral sling can generally be of the type currently in use as an implanted surgical device for treating urinary incontinence, as well as similar slings developed in the future. Examples can be found in the patent literature such as at U.S. Pat. No. 6,911,003 and U.S. Patent Publication No. 2003/0171644. Commercially available slings that could be useful with the articles, techniques, and methods described herein include the sling and implant system available from American Medical Systems, Inc., of Minnetonka, Minn. under the trade designation "MONARC". Urethral slings for placement at the corpus spongiosum can have a widened central support portion for a greater area of contact and greater amount of friction between the central support portion of the sling and the corpus spongiosum. Alternately or additionally, preferred implants can have end portions having certain attachment and/or other performance characteristics.

The sling can be installed using one or more tools to manipulate the urethral sling to a desired position. Examples include curved two-dimensional or three-dimensional tools shaped to allow passage between the lateral incision and the medial incision. End portions of the implant can be connected to or associated with ends of the needles, one for installing an end portion between a left-side lateral incision and to the medial incision, through the obturator foramen. An opposing tool can assist to install the other end portion between the right-side lateral incision and the medial incision, through the obturator foramen. Examples of these types of tools are shown, for example, in U.S. Pat. No. 6,911,003 and in U.S. Patent Publication No. 2003/0171644. Optionally, a single tool may be used to install both sides of the sling through the left and right obturator foramen.

Another method of treating urinary incontinence, and particularly female urinary stress incontinence caused by urethral hypermobility and/or intrinsic sphincter deficiency, includes using a sling system commercially available under the trade designation "SPARC", which is available from American Medical Systems, Inc., of Minnetonka, Minn. This system can be considered to utilize a suprapubic approach in which narrow sling carriers are passed from above the pubic bone to the vagina. A sling is attached to the carriers, such as with certain dilators and their tips or ends, and pulled into place to support the urethra. The sling may be a polypropylene mesh sling material covered with a plastic sheath and having locking connectors attached. The tensioning suture of the system maintains mesh integrity during sling placement of the sling and allows for intra and immediate post-operative tensioning while reducing sling deformation after the plastic sheath is removed.

The invention also relates to devices, methods, and kits that are useful for supporting vaginal tissue in a patient who does not have a uterus, such as an implant that is designed specifically to support the vaginal cuff remaining after removal of the uterus and cervix. The support attaches to posterior vaginal tissue remaining after removal of the uterus and cervix, and attaches also to anatomy to support the vaginal tissue, at or around the sacrum such as to uterosacral ligaments or to the sacrum itself (i.e., to a component of the sacral anatomy). The implant can be attached to a component of the sacral anatomy by any chemical or mechanical attachment such as by an adhesive, a suture, a bone screw or bone anchor, a staple, or any other fastener for tissue or bone. In particular, a surgeon uses an implantable device ("implant") such as a support member, a support strip, or an implant that includes a central support portion attached to two extension portions, to attach to the pericervical ring or vaginal cuff remaining following removal of the uterus and cervix. The implant can be attached to uterosacral ligaments or the sacrum to support the implant and the vaginal vault. The implant may optionally be further supported by attachment of extension portions of the implant to other anatomical features, e.g., a tissue path to an external incision, to thereby further support the vaginal vault.

An implant can include a support portion for attachment to the vaginal cuff. Specific examples of implants can include a support portion designed to be attached to the vaginal cuff, such as to fit around and contact different portions of the vaginal cuff including the apex. The support portion can also include one or more features or areas to attach to a component of the sacral anatomy such as the uterosacral ligaments or the sacrum, to support the vagina, and/or treat or prevent vaginal wall prolapse. The support portion can be designed and installed to prevent possible future enterocele formation.

Optionally, the implant can include one or two or more extension portions attached to the support portion and extending in opposite directions from the support portion. Exemplary implants can include two extension portions including dilators at their ends and extending in opposite directions from a central support portion. The extension portions can be sized and shaped to extend from the central support portion, to be attached to an anatomical position that provides support for the central support portion attached to the vaginal cuff. For example, extension portions can be led through tissue paths from the interior pelvic area to external incisions, with the extension portions becoming ingrown in a manner to support the central support portion of the implant attached to the vaginal cuff.

Extension portions of an implant can be attached anatomically to support the support portion of an implant attached to the vaginal cuff. An exemplary mode of placement of extension portions of an implant can be bilateral passage of the extension portions through tissue paths leading to an external incision, such as an external incision at a perirectal region as discussed in U.S. Patent Publication No. 2005/0245787. This exemplary method includes steps of establishing a first pathway between the external perirectal region of the patient and the region of the ischial spine space in tissue generally on one side of the vaginal cuff, and establishing a second corresponding pathway in tissue on the contralateral side of the vaginal cuff. Exemplary implants as described, including a central support portion and two extension portions, can be attached to the vaginal cuff in such a way as to allow repositioning of the vaginal cuff to an anatomically appropriate location. The extension portions of the implant can then be introduced through the respective bilateral tissue pathways. The extension portions can be adjusted so that the implant and central support portion are located in a therapeutic relationship to the vaginal cuff being supported.

One method of supporting vaginal tissue includes providing a surgical implant comprising a support portion, attaching the support portion to vaginal or cervical tissue remaining upon removal of a uterus, cervix, or both, and attaching the support portion to a component of sacral anatomy. Another method is a transvaginal method of supporting vaginal tissue includes providing a surgical implant, transvaginally attaching the surgical implant to vaginal or cervical tissue remaining after removal of a uterus, cervix, or both, and transvaginally attaching the support portion to a component of sacral anatomy.

In one aspect of the invention, a system for treating pelvic disorders in a patient is provided, the system comprising an implant comprising a support portion and at least one elongated portion extending from the support portion, wherein each elongated portion comprises a dilator at a distal end that is spaced from the support portion. The system further includes an implantation tool comprising an elongated portion and an end portion that is engageable with the dilator, wherein at least one of the dilators comprises a first channel having an engagement feature for positive engagement with the end portion of the implantation tool. The dilator may include a spring-loaded ball extendable into first the channel for positive engagement with the end portion of the implantation tool or may further include a second channel intersecting the first channel, wherein the apparatus further comprises a pin that is slideable within the second channel and within an aperture in the end portion of the implantation tool.

In another aspect of the invention, an apparatus is provided for treating pelvic disorders in a patient, the apparatus comprising a support portion and at least one elongated portion extending from the support portion, wherein each elongated portion comprises a dilator at a distal end that is spaced from the support portion, and wherein the dilator comprises a hinged end portion. In yet another aspect of the invention, a tool is provided for treating pelvic disorders in a patient, the tool comprising a handle and a generally rigid body portion extending from the handle at a proximal end and having a distal end spaced from the handle, wherein the body portion comprises a tip portion that is more flexible than the body portion.

In another aspect of the invention, an implant for treating pelvic disorders in a patient is provided, the implant comprising a support portion comprising a knit mesh having a first density, at least one elongated portion spaced from the support portion comprising a knit having a second density that is less than the first density and at least one connector portion attached to the at least one support portion and to the elongated portion.

BRIEF DESCRIPTION OF THE DRAWINGS

The present invention will be further explained with reference to the appended Figures, wherein like structure is referred to by like numerals throughout the several views, and wherein:

FIG. 5 is a schematic front view of a tool for use in surgical procedures, such as vaginal vault suspensions;

FIGS. 6a-6c are top views of three exemplary embodiments of dilators that can be used with a modular graft kit;

DETAILED DESCRIPTION

Figure 1:
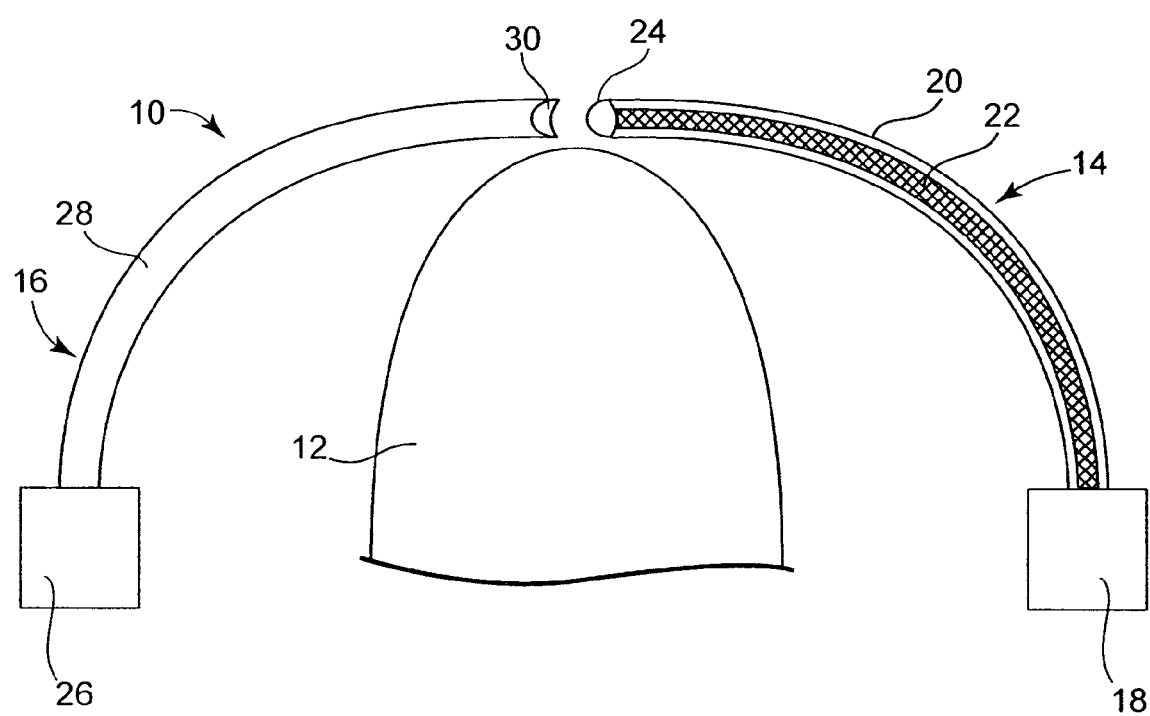
FIG. 1 is a schematic front view of a needle delivery system including atraumatic needle tips positioned generally at the vaginal apex.

The invention relates to devices, methods, and kits, useful for preventing or treating vaginal prolapse, urinary incontinence, and other disorders of the pelvic floor, with the use of implants. The implants can have a wide variety of configurations and connections to implant tools that are designed to be used for different applications.

Exemplary implants can include a central support portion and multiple extension portions, the central support portion being useful to attach to the pelvic tissue to be supported and a component of the sacral anatomy. The central support portion contacts and supports pelvic tissue (e.g., urethral tissue, vaginal tissue, bladder tissue). The central support portion can be sized and shaped to attach to the vaginal cuff at multiple locations such as at a posterior location (e.g., rectovaginal fascia) and an anterior location (e.g., pubovaginal fascia). The central support portion can also be adapted (e.g., sized and shaped) to attach to a component of sacral anatomy such as the uterosacral ligaments or sacrum. As an example, a posterior lobe of a central support portion can include one or more lobe extensions that are of a size and shape to be attached to the sacrum or to one or more uterosacral ligaments.

Extension portions connected to and extending from a central support portion can be useful to attach to other anatomical features to provide support for the central support portion and the tissue to be supported. Extension portions can extend from the central support portion as elongate "arms" or extensions that are attached to other anatomy, such as by extending through a tissue path to an external incision. See, e.g., U.S. Patent Publication No. 2005/0080317, the entirety of which is incorporated herein by reference. The implants can have a number of extension portions (e.g., between 2 and 6 extension portions), depending on where the implant will be used in the body and for what type of procedure the implant will be used. The extension portions can extend through a tissue path to an exterior incision.

The total shape of exemplary implants (e.g., including a central support portion and extension portions) can accommodate surgical placement of the implant to attach to anatomy. For an implant that includes a central support portion and two extension portions, the extension portions can be connected at opposing sides of the central support portion and can extend longitudinally in opposite directions away from the central support portion. For implants that include more than two extension portions extending from a central support portion, the extension portions will be oriented around the perimeter of the central support portion in locations that correspond with anatomical locations in the body where the extensions will be attached or otherwise located.

Materials useful for an implant (e.g., support portion, extension portion, central support portion, etc.) can be any of a variety of synthetic or biologic materials. Exemplary extension and support portions can be prepared from any combination of synthetic and biologic or natural materials. For example, an extension portion or a support portion may be made of a synthetic mesh (e.g., an entire implant can consist of a support portion alone, or a central support portion and extension portions may be made entirely of a one-piece mesh). In other embodiments, exemplary extension portions can be of synthetic mesh and a central support portion can be of a synthetic or biologic tissue material. Components of a multi-piece or multi-material implant may be pre-attached or pre-assembled. For example, the portions of an implant can be attached during manufacture, so a surgeon is not required to spend significant time cutting, connecting, or otherwise assembling the pieces of an implant prior to a surgical installation procedure.

A synthetic implant material can be any synthetic material that is useful in an implantable surgical device, such as a biocompatible polymeric material or a biocompatible non-polymeric synthetic material. Examples of useful polymeric materials that may be useful in a polymeric mesh include thermoplastic polymeric materials such as polyolefins (e.g., polypropylenes), polyurethanes, acetel materials, Teflon® materials, and the like; thermoset materials such as silicones; and materials that are otherwise curable, e.g., that can be cured by ultraviolet radiation or chemical reactions, including curable materials such as curable urethanes, epoxies, acrylates, cyanoacrylates, and the like. Any of these materials may be homopolymers, copolymers, or a blend or other combination of homopolymers, copolymers, or both. Other suitable synthetic materials include metals (e.g.; silver filigree, tantalum gauze mesh, and stainless steel mesh).

A synthetic implant material may be in any form, such as a continuous, solid, or semi-continuous (e.g., perforated) film; or in the form of combined fibers or strands, such as a braided, knit, tied, mesh, woven, non-woven, or fabric-type of material; or combinations of these. Certain embodiments of implants include a synthetic implant portion in the form of a polymeric mesh material. The mesh material includes one or more woven, knitted or inter-linked polymeric filaments or fibers that form multiple fiber junctions throughout the mesh. The fiber junctions may be formed via weaving, knitting, braiding, joining, ultrasonic welding or other junction forming techniques, including combinations thereof, leaving openings or pores ("interstices") between elements of the fibers. The size of the interstices mesh may be sufficient to allow tissue in-growth and fixation within surrounding tissue.

Many different types of synthetic film and mesh materials are known and may be suitable for use as a portion or piece of an implant such as an extension portion or a central support portion. These materials may be prepared from biocompatible materials that may be bioabsorbable or non-bioabsorbable, e.g., in the form of mesh materials. Suitable materials include cotton, linen, silk, polyamides (polyhexamethylene adipamide (nylon 66), polyhexamethylene sebacamide (nylon 610), polycapramide (nylon 6), polydodecanamide (nylon 12), and polyhexamethylene isophthalamide (nylon 61), and copolymers and blends thereof), polyesters (e.g., polyethylene terephthalate, polybutyl terephthalate, copolymers and blends thereof), fluoropolymers (e.g., polytetrafluoroethylene and polyvinylidene fluoride), polyolefins (e.g., polypropylene, including isotactic and syndiotactic polypropylene and blends thereof, as well as blends composed predominantly of isotactic or syndiotactic polypropylene blended with heterotactic polypropylene, and polyethylene), silicone, polygalactin, Silastic, polycaprolactone, polyglycolic acid, poly-L-lactic acid, poly-D-L-lactic acid and polyphosphate esters.

Commercial examples of polymeric materials for use in an implant include MARLEX (polypropylene) available from Bard of Covington, R.I.; PROLENE (polypropylene) and PROLENE Soft Polypropylene Mesh or Gynemesh (nonabsorbable synthetic surgical mesh), both available from Ethicon, of New Jersey; MERSILENE (polyethylene terephthalate) hernia mesh also available from Ethicon; GORE-TEX (expanded polytetrafluoroethylene) available from W. L. Gore and Associates, Phoenix, Ariz.; INTEPRO™ polypropylene materials, and the polypropylene material used in the commercially available SPARC® sling system, each available from American Medical Systems, Inc. of Minnetonka, Minn. Commercial examples of absorbable materials include DEXON (polyglycolic acid) available from Davis and Geck of Danbury, Conn., and VICRYL available from Ethicon.

Suitable non-synthetic (biologic) implant materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium, and fascia lata.

According to certain embodiments of implants, various additional components and features can be incorporated for added utility or convenience, such as components and features that facilitate installation of a device during a surgical procedure. For instance, a tensioning member (e.g., suture) may be attached to an implant along a portion or entire length of an extension member for use in adding tension or in positioning an implant or a portion (e.g., extension) of an implant. Alternately or in addition, an exemplary implant may include a removable sheath such as a plastic, transparent elongate tube, etc., that can cover a portion or entire length of an extension portion of an implant to facilitate installation by allowing a surgeon to apply tension or pressure on the sheath to indirectly apply pressure or tension to the extension portion. Additionally or alternately, extension portions of an implant may include a connector or "dilator" tip at an end of an extension member distal from a central support member, the connector being able to cooperate with an insertion tool (e.g., needle, tunneler, etc.) during a surgical procedure to either push or pull the connector using the end of the insertion tool. For example, a tip may be a rigid plastic tip or "dilator" constructed to attach to an end of an elongate insertion tool by snapping or otherwise securing to the end of the tool. The tool can then be used to push or pull the connector through a tissue passage to also bring the extension portion of the implant through the tissue passage. Variations in these dilators and insertion tools, including methods and devices to provide easier attachment between the components, are described herein, in accordance with the invention.

Referring now to the Figures, wherein the components are labeled with like numerals throughout the several Figures, and initially to FIG. 1, one preferred configuration of a needle delivery system 10 is illustrated, as positioned relative to a vaginal apex 12. Delivery system 10 generally includes a stylette needle 14 and a second needle 16. Needle 14 includes a handle 18, a body portion 20 having a mesh material 22 housed therein, and a distal tip or dilator 24. Needle 16 includes a handle 26, a body portion 28, and a distal tip or dilator 30. This system 10 is used to help physicians to visualize and/or insert a mesh to the vaginal apex for a vault suspension in a blinded approach. Body portions 20, 28 of the needles each are designed to have an appropriate length and curvature to provide access to the vaginal apex or other area of the anatomy where such a system can be used. System 10 may also be referred to as an apical suspension kit in which preloaded mesh 22 and needle 14 are delivered together to the surgical site (e.g., the vaginal apex). In the surgical technique, distal tips 24, 30 are aligned with each other, such as in a self-aligning arrangement. Distal tips 24, 30 are then mated or engaged with each other at the apex, with mesh 22 pre-attached to a dilator grommet at the distal tip 24. Distal tips 24, 30 may engage with each other in a number of ways, such as with the snap-fit type of connection illustrated in FIG. 1, or with another type of positive-engagement connection.

Once tips 24, 30 engage with each other, both needles 14, 16 can be pulled out, thereby pulling mesh 22 out of body portion 20 of needle 14 via the dilator grommet connection at distal tip 24. In this way, a physician does not need to feed a dilator/mesh material individually through the vaginal orifice to snap onto a needle. The mesh material 22 can then be attached to the vaginal cuff, for example.

Figure 2:
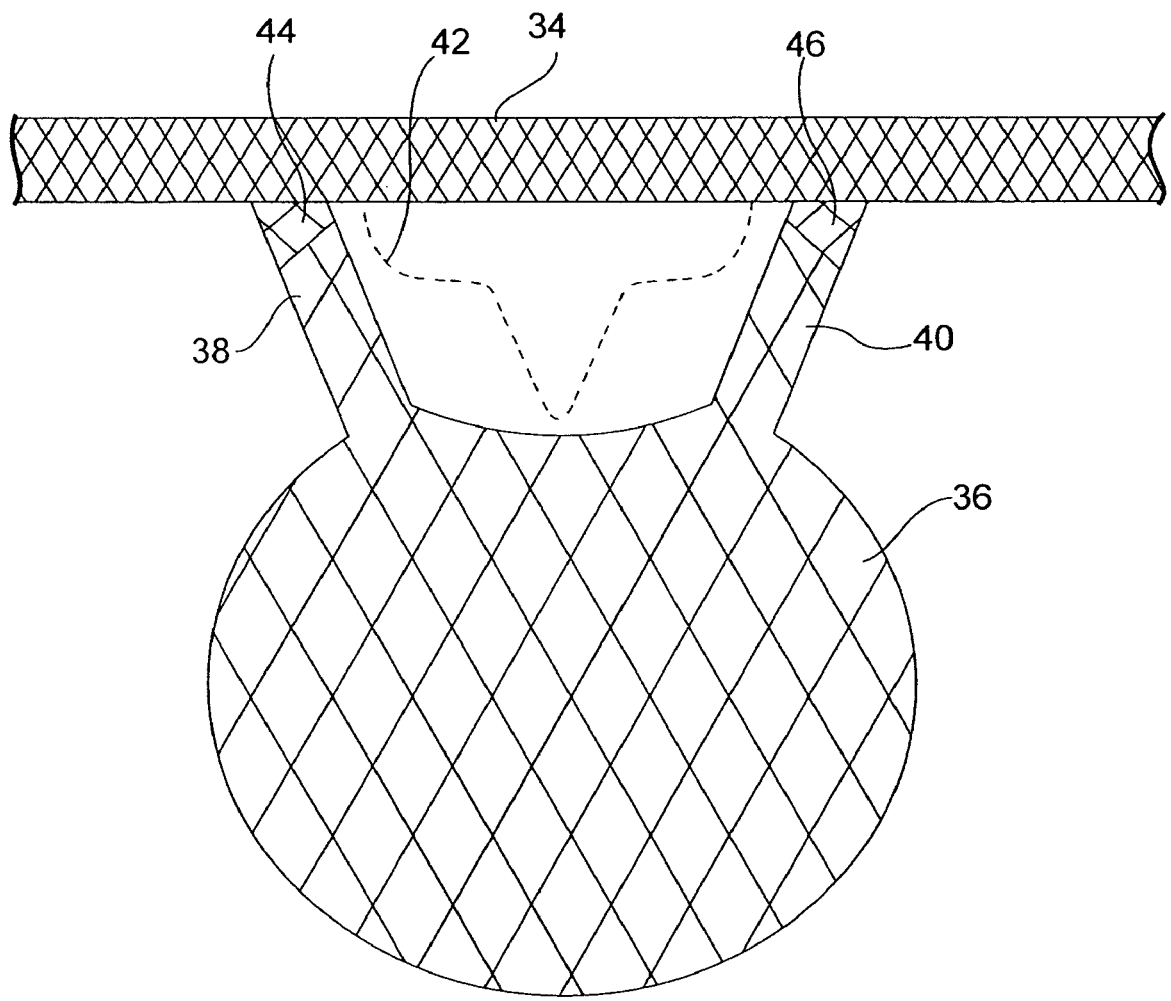
FIGS. 2-4 are schematic front views of a portion of three different exemplary surgical slings in accordance with the invention, each of which illustrates a different attachment between a support portion and at least one extension portion.
Figure 3:
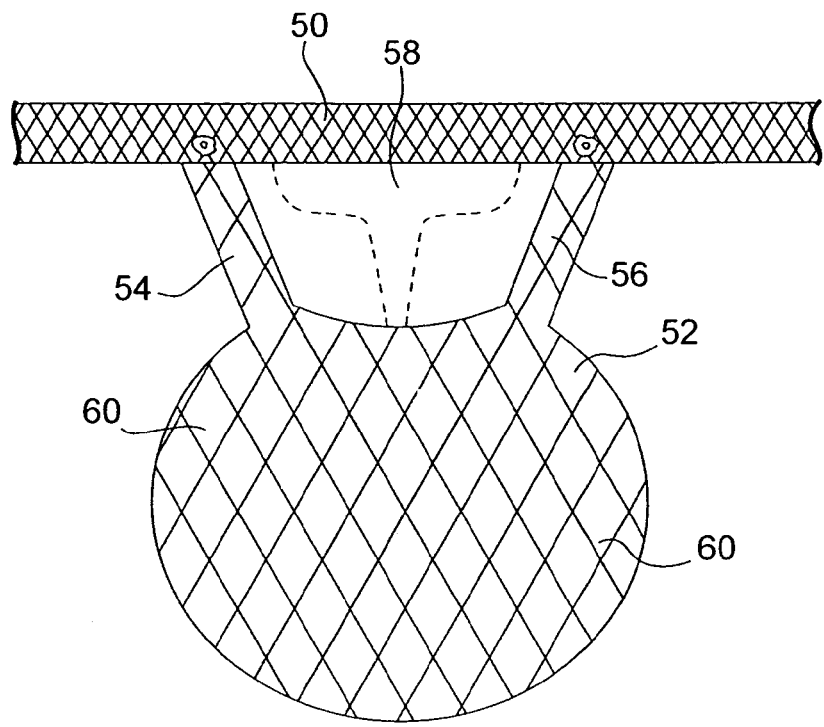
Figure 4:
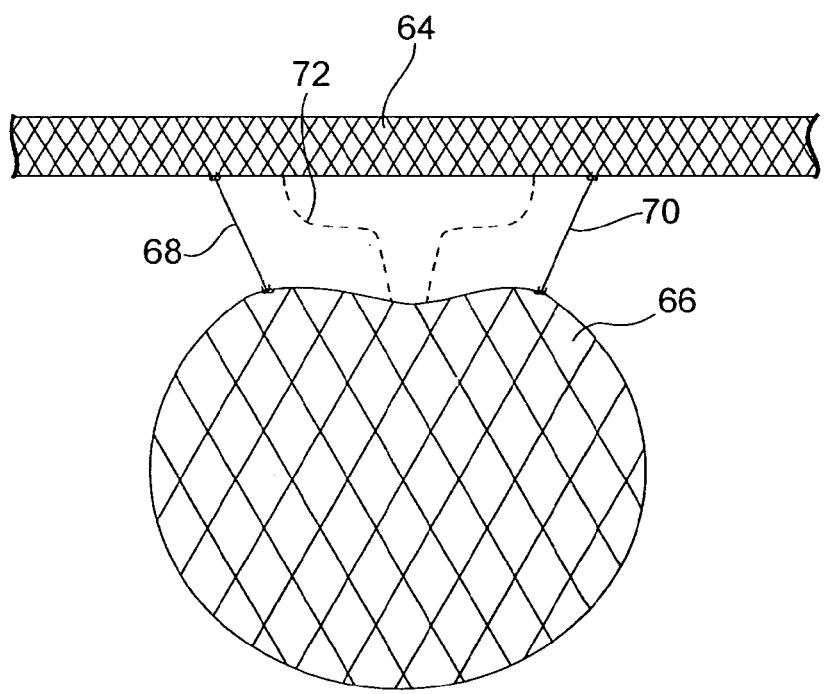

FIGS. 2-4 illustrate different attachment methods and configurations for connecting surgical sling portions to each other. First, FIG. 2 illustrates a first mesh portion 34, which may be a mesh of a SPARC implant, for example, and a second mesh portion 36, which may be a softer or looser density mesh than that of first mesh portions 34 (e.g.; a non-resorbable synthetic prosthesis material, such as is commercially available from Johnson & Johnson of New Brunswick, N.J. under the trade designation "Gynemesh"). Mesh 36 is shown as attached to first mesh portion 34 via two extensions 38, 40, between which a bladder neck 42 is positioned. Extensions 38, 40 meet mesh portion 34 at transition areas 44, 46, respectively, which are knitted areas that provide a transition between first mesh portion 34 and the relatively more open and softer mesh material of second mesh portions 36. This connection may be performed by a knitting machine, for example, and is intended to provide an area with a mesh that has intermediate properties as compared to mesh 34 and mesh 36.

Extensions 38, 40 may make a bioresorpable attachment between first and second mesh portions 34, 36 in order to have a relatively rigid connection during the implantation process for ease of use. However, this rigid connection can disappear or degrade before tissue in-growth to minimize or avoid constraint of the bladder neck when in-growth takes place.

FIG. 3 illustrates another first mesh portion 50, which may be a mesh of a SPARC implant, for example, and a second mesh portion 52, which may again be softer density mesh than that of first mesh portion 50. Mesh portion 52 is attached to mesh portion 50 via two extensions 54, 56, between which a bladder neck 58 is positioned. Extensions 54, 56 are attached to first mesh portion 50 with an attachment method that does not involve additional knitting, as with the system of FIG. 2, but instead is attached with a spot weld, laser weld, bioarc suture attachment, ultrasonic welding, or the like. Second mesh portion 52 further includes at least one anatomical landmark or sizing demarcation 60, such as colored sutures and/or ink markings. Demarcation(s) 60 allow the surgeon to customize the graft to each patient's particular anatomy.

FIG. 4 illustrates another first mesh portion 64, which may be a mesh of a SPARC implant, for example, and a second mesh portion 66, which may again be a softer or looser density mesh than that of first mesh portion 64. Mesh portion 64 is attached to mesh portion 66 via two extensions 68, 70, between which a bladder neck 72 is positioned. Extensions 68, 70 are provided as loose suture attachments that can be knotted (such as at an assembly area) at one or both of their ends to the first and second mesh portions 64, 66. These extensions 68, 70 may be made of a permanent or bioresorpable material, and are designed to avoid rigid attachment, which can thereby alleviate possible bladder neck funneling constriction. That is, if a bioresorpable suture is used, it will absorb before permanent in-growth to avoid bladder neck constriction.

With respect to the embodiments of FIGS. 2-4, a flexible neck attachment from the first mesh portion (e.g., an incontinence sling) to the second mesh portion (e.g., an anterior patch) will allow for natural dynamics of the bladder neck and vaginal wall to act independently. If a bioresorpable suture or mesh is used to allow for ease of implantation, the attachment will be temporary since the material will absorb quickly before the body relies on in-growth. This may prevent scar tissue buildup, which may in turn prevent bladder neck funneling.

FIG. 5 illustrates a needle 80 for use particularly in vaginal vault suspensions, although it may also be useful in other applications. Needle 80 includes a relatively rigid or non-malleable shaft 82, a handle 84, and a tip portion 86. Needle 80 provides the surgeon with the ability to change the orientation of at least a portion of the needle once it is positioned within the patient. This can be particularly advantageous, for example, in procedures where the surgical instrument first passes through a relative straight body opening, but then the end portion of the needle needs to be bent or angled differently to access a certain portion of the anatomy. Shaft 82 has a preset shape that is designed to move through the fascia muscle, for example. Tip 86 is relatively flexible or malleable as compared to shaft 82, and is provided so that it can be bent or redirected as compared to shaft 82 to make it easier to insert a mesh to the vaginal apex for vault suspension. This is accomplished through a flexible and/or malleable and/or steerable tip on the end of a needle portion having a pre-set shape (e.g., shaft 82) to snap or otherwise attach onto a dilator to get the mesh anchored to the vaginal apex.

Tip portion 86 can be made of a single piece of relatively flexible material, for example, and/or may include another configuration that uses less flexible materials arranged in a way that allows articulation between adjacent portions (i.e., articulating knuckle joints) or could include a steerable coil. An alterative tip portion is illustrated as connection 88, which includes a series of snap-fit links 90 coupled to each other in such a way to provide flexibility to the tip portion. In any case, the tip portion of needle 80 allows for bending to an appropriate flexure radius for accessing the desired area of the patient's anatomy.

With regard to dilators used with slings in surgical procedures of the type described herein, and in accordance with the invention, a modular system is provided for use with a modular graft kit. A modular graft kit may include several different needles to be used by a physician, depending on the approach taken or where the graft may be attached. In order to make it easier for the physician to match each needle to its corresponding dilator, each dilator can be keyed or coded in such a way that it is identifiable to be associated with a certain needle tip. In one example, a dilator and needle that are intended to be used together can each have a portion that is the same color, for easy visual identification of associated needles and dilators. In another example, which is illustrated in FIGS. 6a-6b, dilators are keyed differently for each needle attachment to prevent using the wrong needle with a particular dilator. This type of system can be used as a kit having multiple surgical implants (with dilators) and multiple tools, in which would not be possible for a surgeon to inadvertently attach a needle tip to a surgical implant that is supposed to be used in a different area of the patient. In this exemplary embodiment, FIG. 6a illustrates a profile of a first dilator 90, which may be used in a posterior surgical approach, for example; FIG. 6b illustrates a profile of a second dilator 94, which may be used in a transobturator surgical approach, for example; and FIG. 6c illustrates a profile of a third dilator 97, which may be used in a suprapubic surgical approach, for example, although the tools can be provided for different surgical techniques than listed. As shown, dilator 90 includes an opening 92 having a first shape, dilator 94 includes an opening 96 having a second shape, and dilator 97 includes an opening 98 having a third shape. First, second, and third shapes 92, 96, and 98 are at least slightly different from each other, and preferably will only allow attachment of a particular needle tip. Thus, if a surgeon were to perform a surgery that involves a transobturator surgical approach, for example, the surgeon could select the needle to be used in the surgery, which would have a needle tip to which only a certain dilator (e.g.; second dilator 94) would be attachable. The profile of each of the dilators can also be different sizes.

In cases where a system allows use of multiple dilators with the same needle (i.e., in systems where multiple implants have the same dilator configuration), it is possible that a physician can insert the wrong needle onto the dilator. In these cases, a universal, quick release dilator can be provided that would allow the physician to remove the needle from a dilator if it is inserted onto the incorrect needle. This universal dilator is configured to prevent twisting of the mesh and provide easy removal if the wrong dilator is attached to a needle. This concept would also allow aid in providing inventory management since the kits can be provided with generic dilators that would fit onto any needle tip.

In accordance with another aspect of the invention, needle systems are provided that include features at the needle tip that allow for easy advancement of the needle through the patient's tissue, such as can be used with the systems designated by the trade designations "SPARC" and "MONARC", both of which are commercially available from American Medical Systems, Inc., of Minnetonka, Minn. These needle systems allow for a more blunt/atraumatic passage of the needle, and further have the ability to engage securely with corresponding dilators. These needle systems are particularly advantageous in areas of the body where a sharp needle tip will be in close proximity to structures that are particularly susceptible to being damaged, for example. For these applications, a needle head or tip is provided that is at least slightly larger than the elongated portion of the needle, but that is relatively blunt or rounded to allow for safer passage of the needle through the body tissues. The slightly larger size of the needle head or tip can provide a larger radius, which in turn can provide for smoother passage through the tissue.

Figure 7:
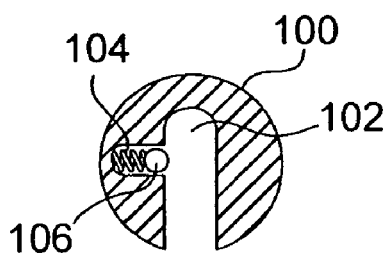
FIG. 7 is a cross-sectional front view of a dilator portion of a surgical implant.
Figure 8:
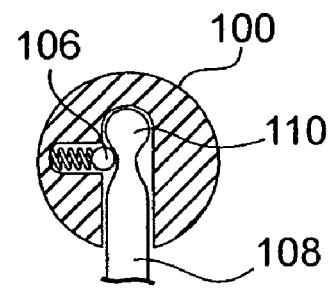
FIG. 8 is a front cross-sectional view of a needle end engaged with the dilator of FIG. 7, with a spring-loaded ball retaining the needle tip in position relative to the dilator.

One example of such a needle system is illustrated in FIGS. 7 and 8, where FIG. 7 illustrates a dilator 100 having an inner channel 102 that extends through at least a portion of dilator 100. Dilator 100 further includes a spring 104 (shown here in a retracted position, for clarity purposes) and a ball 106 that allow for a spring-loaded connection with the needle 108, as shown in FIG. 8. In particular, a ball end 110 of needle 108 is sized so that it can move ball 106 to compress spring 104 when it is being pressed into the channel 102, until ball 110 moves beyond the spring 104 and ball 106. Due to the force of spring 104, ball 106 will then engage with needle 108 below ball 110, thereby retaining needle 108 in this position relative to dilator 100. Thus, spring 104 should be capable of providing sufficient force to maintain needle 108 in its engaged configuration.

Figure 9:
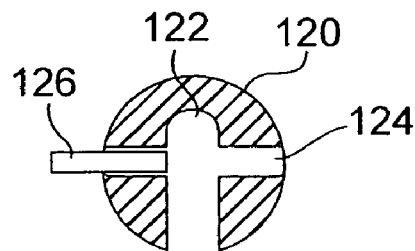
FIG. 9 is another cross-sectional front view of a dilator portion of a surgical implant.
Figure 10:
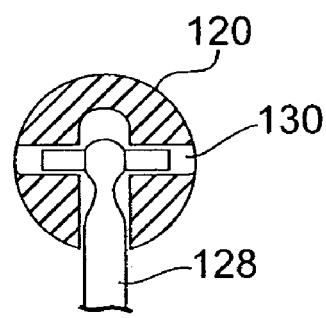
FIG. 10 is a front cross-sectional view of a needle end engaged with the dilator of FIG. 9, with a sliding pin retaining the needle tip in position relative to the dilator.

Another example of a needle system similar to that of FIGS. 7 and 8 is illustrated in FIGS. 9 and 10, where FIG. 9 illustrates a dilator 120 having a first inner channel 122 that extends through at least a portion thereof, and a second inner channel 124 that intersects channel 122. Channel 124 may be essentially perpendicular to channel 122, as shown, or may instead be at an angle relative to channel 122. Dilator 120 further includes a sliding pin 126 that allow for a positive engagement with a needle 128 having an end 130, as shown in FIG. 10. In particular, needle 128 can be pressed into channel 122 of dilator 120 until its end 130 is positioned so that a hole through it (not visible in this figure) is aligned with channel 124. Sliding pin 126 can then be slid through channel 124 and the hole through end 130 of needle 128, thereby providing a positive engagement between sliding pin 126 and needle 130. Channel 124 can extend all or part of the way through dilator 120, but should be long enough so that the sliding pin 126 can sufficiently engage with the needle 130. This system may include multiple sliding pins, if desired, or may include multiple needle retention configurations, such as a system that includes both a spring loaded ball, as in FIGS. 7 and 8, in combination with a sliding pin mechanism, as in FIGS. 9 and 10, for example.

Figure 11:
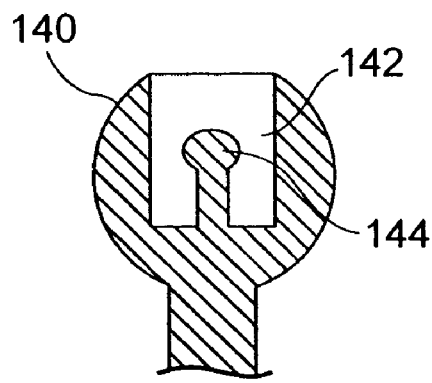
FIG. 11 is a front cross-sectional view of a needle tip including a dilator-retaining feature.
Figure 12:
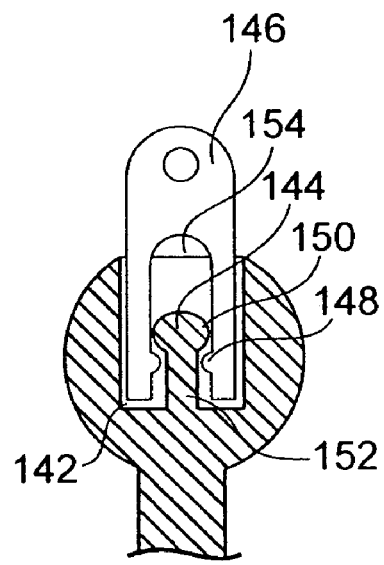
FIG. 12 is a front cross-sectional view of the needle tip of FIG. 11, along with a dilator portion of a surgical implant positioned therein.

Another example of a needle system engagement configuration is illustrated in FIGS. 11 and 12. FIG. 11 illustrates a needle tip 140 with an inner channel 142 having an extension 144, which functions as a dilator-retaining feature. FIG. 12 illustrates a dilator portion 146 of a surgical implant positioned within inner channel 142. Dilator portion 146 includes at least one extension 148 that engages with the extension of inner channel 144 in a number of different ways, one of which is illustrated in FIG. 12. In particular, extension 144 includes an enlarged portion 150 that has a larger cross-section than the area 152 immediately below it, and dilator 146 includes a channel 154 with at least one extension 148. When dilator portion 146 is pushed into needle tip 140, the extension(s) 148 move or flex away from the enlarged portion 150 until the enlarged portion 150 is on the opposite side of the extension (s) 148, thereby keeping the dilator portion 146 securely engaged with the needle 140. Alternatively, a sliding pin arrangement may be used with this general configuration.

Figure 13:
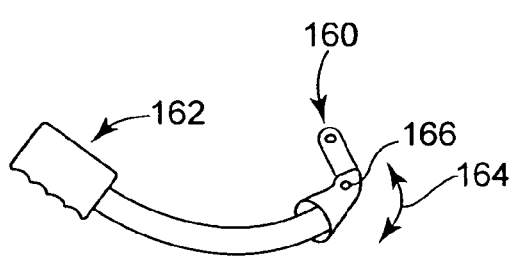
FIG. 13 is a front view of an exemplary dilator or end portion of a surgical implant, in accordance with the invention.
Figure 14:
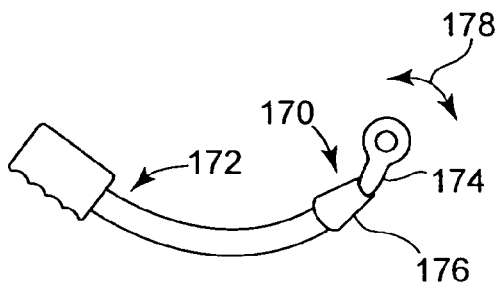
FIG. 14 is a front view of another exemplary dilator or end portion of a surgical implant, in accordance with the invention.

FIGS. 13-17 illustrate dilator and needle tip variations that are particularly useful in low-clearance anatomy applications, such as for accessing the area of the vaginal vault, such as with the systems commercially available under the trade designation "SPARC" or "MONARC" from American Medical Systems, Inc., of Minnetonka, Minn. In at least some of the embodiments, a needle tip can be attached to a dilator from the side, which is particularly beneficial in areas where the surgeon has limited access to the area. FIG. 13 illustrates a dilator 160 engaged with a needle 162, where the dilator 160 is hinged to be able to move in the directions indicated by arrow 164, such as about one or more hinge pins 166. FIG. 14 illustrates a dilator 170 engaged with a needle 172, where the dilator 170 includes a socket portion 176 about which a ball portion 174 can rotate, although these portions may be interchanged. Dilator 170 can thus move in the directions indicated by arrow 178 through a ball-in-socket type of connection. These hinged dilators can allow easier attachment of the dilator to the needle, and can also more easily follow a relatively tortuous needle path, particularly during withdrawal of the needle. In addition, these hinged or moveable dilators can be provided with a locking function to allow the dilator to be fixed in a certain position, then released to be moveable, such as to do a perpendicular connection between a dilator and needle tip.

Figure 15:
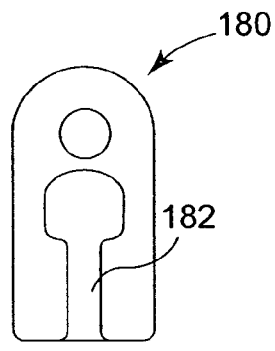
FIG. 15 is a front view of another exemplary dilator or end portion of a surgical implant, in accordance with the invention.
Figure 16:
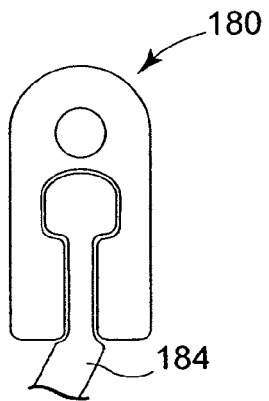
FIG. 16 is a front view of the dilator tip of FIG. 15, with a needle end engaged with the dilator.

FIG. 15 illustrates a dilator 180 having a channel 182 extending at least partially through its length. In FIG. 16, a needle 184 is engaged within the channel 182. Dilator 180 can be snapped onto the needle 184 from the side instead of the top, then further connected with an axial movement of the needle relative to the dilator, which allows for an alternative attachment path that is advantageous in tighter spaces.

Figure 17:
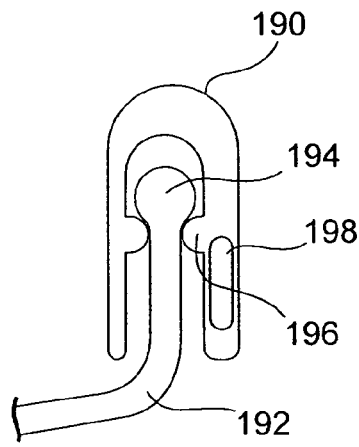
FIG. 17 is a front view of another exemplary dilator of the invention, with a needle end engaged therewith.

FIG. 17 illustrates another dilator 190 engaged with a needle 192. Needle 194 engages with extensions 196 of dilator 190 to retain the needle 194 relative to dilator 190 in a similar manner to the engagement configuration described above relative to FIG. 13. Dilator 190 further includes a hole 198 for retaining a mesh material that can position the mesh beside the needle rather than above the needle, which allows the system to be at least slightly shorter or more compact.

In another aspect of the invention, a tool is provided that a physician can use to determine the size of mesh and/or the shape of a mesh needed for a patient's anatomy. This tool can be used in combination with a cape or support portion (e.g., with a support portion of a SPARC device) that has demarcations on the mesh that identifies a shape and size that a physician can trim. The tool can be a pessary-like and/or Baden speculum tool that identifies the size and shape of a mesh needed to repair a cystocele defect, for example. In this way, the physician would not need to guess at what type of shape or size the graft would need to be for a cystocele repair, for example. In other words, the shape and size of a patient is determined before the mesh is trimmed.

Surgical installation using methods and devices described herein can involve methods that are laproscopic, abdominal (involving an abdominal incision) or transvaginal. In exemplary transvaginal methods, following attachment of a central support portion of an implant to the vaginal cuff, extension portions of an implant can be secured to support the central support portion and the vaginal cuff. This can be done, e.g., by establishing tissue pathways to exterior incisions and leading the extension portions through the tissue pathways.

Exemplary methods of providing tissue pathways from the vaginal region to external incisions, for installing an implant to support vaginal tissue, are described in U.S. Patent Publication No. 2005/0245787, entitled "Method and Apparatus for Treating Pelvic Organ Prolapse". Other methods will also be useful. As described in the referenced patent application, two tissue pathways are established between the external perirectal region and the region of the ischial spine. Tools useful for this procedure can be straight or curved needles, optionally including a tip with an adapter that cooperates with a tip or dilator at the end of extension portions of the implant, to allow the dilator of the end portion to be attached to the tip of the needle to lead the dilator and extension portion to a desired location, e.g., through a tissue path to an external incision. The dilator variations described herein may be used alone or in combination with each other for a single needle system, as desired.

A useful needle can be generally curved or arcuate. A variety of needle designs may be used including, without limitation, straight, bent, curved, arc-shaped, Stamey, Raz and other configurations. Another tool that may be useful is a tunneler (e.g., the IVS Tunneler device available commercially from Tyco), which can also be inserted from an external incision to attach to an end of an extension portion to allow the extension portion to be led from the pelvic region to an external location.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. An apparatus for treating pelvic disorders in a patient, the apparatus comprising:
   a support portion; and
   at least one elongated portion extending from the support portion, wherein each elongated portion comprises a dilator at a distal end that is spaced from the support portion;
   wherein the dilator comprises a hinged end portion that comprises a first structure comprising a socket rotatably connected to a second structure comprising a ball.

2. A system for treating pelvic disorders in a patient, the system comprising:
    an implant comprising a support portion and at least one elongated portion extending from the support portion, wherein each elongated portion comprises a dilator at a distal end that is spaced from the support portion; and
    an implantation tool comprising:
        a handle; and
        a generally rigid body portion extending from the handle at a proximal end and having a distal end spaced from the handle,
        wherein the body portion comprises a tip portion that is more flexible than the body portion, wherein the tip portion comprises multiple tip segments, and wherein at least one tip segment is moveably connected to an adjacent tip segment;
    wherein at least one of the dilators comprises a first channel having an engagement feature for positive engagement with the tip portion of the implantation tool.

3. An implant for treating pelvic disorders in a patient, the implant comprising:
    a support portion comprising a knit mesh having a first density;
    at least one elongated portion spaced from the support portion comprising a knit having a second density that is less than the first density;
    at least one connector portion attached to the at least one support portion and to the elongated portion; and
    a transitional area at an end of at least one connector portion adjacent the support portion, the transitional area having a knit density that is less than the first density and greater than the second density.

* * * * *